(12) United States Patent
Zanelli

(10) Patent No.: US 6,546,276 B1
(45) Date of Patent: Apr. 8, 2003

(54) ULTRASONIC BASED DETECTION OF INTERVENTIONAL MEDICAL DEVICE CONTACT AND ALIGNMENT

(76) Inventor: Claudio I. Zanelli, 2100 Prospect St., Menlo Park, CA (US) 94025

(*) Notice: Subject to any disclaimer, the term of this patent is extended or adjusted under 35 U.S.C. 154(b) by 182 days.

(21) Appl. No.: 09/660,056

(22) Filed: Sep. 12, 2000

(51) Int. Cl.[7] .............................................. A61B 5/055
(52) U.S. Cl. ....................... 600/424; 600/407; 600/448; 600/459; 600/466
(58) Field of Search ................................ 600/424, 439, 600/407, 448, 459, 462, 466

(56) References Cited

U.S. PATENT DOCUMENTS

| | | | |
|---|---|---|---|
| 3,978,714 A | * 9/1976 | Shraiber et al. | 73/625 |
| 4,054,053 A | * 10/1977 | Yamamoto et al. | 73/610 |
| 4,472,742 A | * 9/1984 | Hasegawa et al. | 348/232 |
| 4,583,393 A | * 4/1986 | Sweet | 73/32 A |
| 4,658,817 A | 4/1987 | Hardy | 128/303.1 |
| 4,914,952 A | * 4/1990 | Miyajima et al. | 73/598 |
| 4,917,097 A | 4/1990 | Proudian et al. | 128/662.06 |
| 4,936,281 A | 6/1990 | Stasz | 128/660.03 |
| 4,961,173 A | * 10/1990 | Sehr et al. | 367/907 |
| 5,109,830 A | 5/1992 | Cho | 128/4 |
| 5,109,859 A | 5/1992 | Jenkins | 128/662.03 |
| 5,196,006 A | 3/1993 | Klopotek et al. | 606/12 |
| 5,313,950 A | 5/1994 | Ishikawa et al. | 128/662.06 |
| 5,319,611 A | * 6/1994 | Korba | 367/909 |
| 5,377,682 A | 1/1995 | Ueno et al. | 128/660.1 |
| 5,409,000 A | 4/1995 | Imran | 128/642 |
| 5,544,656 A | 8/1996 | Pitsillides et al. | 128/661.04 |
| 5,662,124 A | 9/1997 | Wilk | 128/898 |
| 5,724,975 A | 3/1998 | Negus et al. | 128/661.09 |
| 5,768,939 A | * 6/1998 | Quayle et al. | 73/290 V |
| 5,893,848 A | 4/1999 | Negus et al. | 606/41 |
| 6,019,725 A | * 2/2000 | Vesely et al. | 128/916 |
| 6,019,726 A | 2/2000 | Webb | 600/459 |
| 6,024,703 A | 2/2000 | Zanelli et al. | 600/437 |
| 6,030,377 A | 2/2000 | Linhares et al. | 606/7 |
| 6,086,534 A | 7/2000 | Kesten | 600/439 |

FOREIGN PATENT DOCUMENTS

| | | | |
|---|---|---|---|
| DE | 195 37 084 | 4/1997 | |
| DE | 196 06 610 | 8/1997 | |
| EP | 0 876 796 | 11/1998 | |
| JP | 9-38089 | 2/1997 | ............ A61B/8/12 |
| WO | WO 97/25101 | 7/1997 | |
| WO | WO 98/17185 | 4/1998 | |
| WO | WO 98/30144 | 7/1998 | |
| WO | WO 98/38916 | 9/1998 | |

OTHER PUBLICATIONS

K K Shung and B McGuire, "Development of Ultrasonically Marked Needle for Ultrasonically Guided Biospy", Mar. 1989, IEEE Processing of the 1989 Bioengineering Conference, 119–120.*

G.L. Wojcik, D.K. Vaughan, N.N. Abboud, J. Mould Jr., "Electromechanical Modeling Using Explicit Time–Domain Finite Elements", Preprint of the final article that appeared in *IEEE 1993 Ultrasonics Symposium Proceedings*, vol. 2, pp. 1107–1112.

* cited by examiner

Primary Examiner—Marvin M. Lateef
Assistant Examiner—Runa Shah Qaderi
(74) Attorney, Agent, or Firm—Shirley L. Church; James F. Feeney

(57) ABSTRACT

A method and apparatus for remotely monitoring the location of an interventional medical device (IMD) using ultrasonic signals. Both the proximity and alignment of the IMD are calculated from ultrasound signals reflected off the tissue surface. The inclusion of an offset between the distal end of the IMD and the ultrasound transducer enables accurate position and alignment monitoring of when the IMD is in contact with, or very close to, the tissue surface. The timing of the reflected signal is used to measure proximity or contact. A comparison of the strength between multiple reflected signals is used to measure the alignment of the IMD in 3D space or perpendicularity to a given surface. The present invention may be used as a location indicator within a wide variety of IMDs, and in a wide variety of medical procedures.

19 Claims, 7 Drawing Sheets

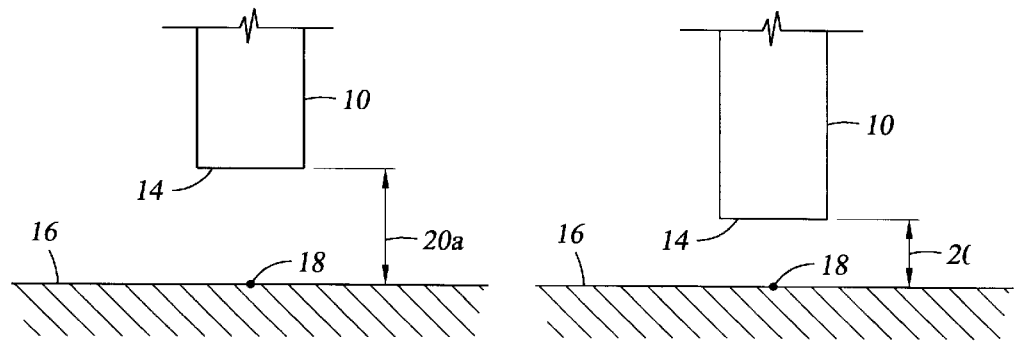
Fig. 2A    Fig. 2B
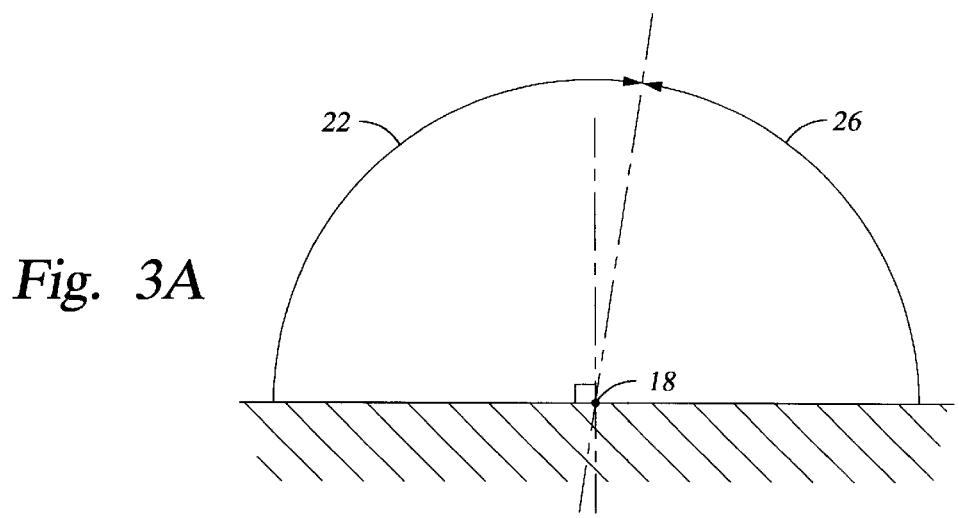
Fig. 3A
Fig. 3B

PROXIMITY

PERPENDICULAR TO AXIS 1

PERPENDICULAR TO AXIS 2

TIME OR DISTANCE

ULTRASONIC BASED DETECTION OF INTERVENTIONAL MEDICAL DEVICE CONTACT AND ALIGNMENT

FIELD OF THE INVENTION

The present invention relates to monitoring interventional medical devices (IMDs). More particularly, the present invention relates to an ultrasonic system of monitoring the proximity and alignment of the IMD relative to a tissue surface.

BACKGROUND OF THE INVENTION

Interventional medical devices (IMDs), such as catheters and surgical lasers are used for many medical procedures. Laparoscopy, the insertion of a fiber optic instrument into the abdomen, is just one relatively common type of IMD procedure. Minimally invasive surgery (MIS) is a term that, as used in this disclosure, encompasses a broader range of such procedures, and in which an IMD is introduced into the patient through a relatively small incision. A major problem inherent with the use of IMDs in MIS procedures is detecting the current location and orientation of the IMD, and remotely guiding it within a patient. It would be desirable to have an apparatus or method that assisted in precisely determining the location and orientation of a wide range of IMDs. It would be particularly desirable to have an apparatus or method for determining when the distal end of the IMD is in contact with and perpendicular to a tissue surface.

U.S. Pat. No. 5,109,859 issued to Jenkins on May 5, 1992 (the '859 patent), discloses an ultrasound guided laser for use in angioplasty. The '859 patent is specifically directed at a method of imaging the lateral walls of arteries for laser ablation procedures and can not easily be adapted to function with a wide range of IMDs.

U.S. Pat. No. 5,313,950 issued to Ishikawa, et al. on May 24, 1994 (the '950 patent), discloses an ultrasonic probe for providing images in hollow objects such as blood vessels. The '950 patent, like the '859 patent, creates images at 90° to the longitudinal axis of the IMD. This lateral imaging provides little data for determining IMD alignment and indicating when the distal end of the IMD is in contact with a tissue surface.

U.S. Pat. No. 5,377,682 issued to Ueno, et al. on Jan. 3, 1995 (the '682 patent) also teaches an ultrasonic probe for imaging perpendicular to the longitudinal axis. Again, there is no description which assists in determining alignment of the probe and indicating when the distal end of the IMD is in contact with a tissue surface.

U.S. Pat. No. 5,893,848 issued to Negus, et al. on Apr. 13, 1999 (the '848 patent), teaches a gauging system for monitoring the depth of an IMD as it penetrates into heart tissue. However, the '848 patent does not provide data on the proximity of the IMD to the tissue surface prior to penetrating the surface, nor does it indicate the angle of the IMD relative to the tissue surface.

U.S. Pat. No. 6,024,703 issued to Zanelli, et al. on Feb. 15, 2000 (the '703 patent), measures the distance between the distal end of the IMD and the tissue surface both prior to contacting the surface and after penetrating the surface. This invention is primarily directed at measuring the distance between a laser IMD that has penetrated the tissue surface and the rear surface of that tissue. It is not as well suited for providing positional data prior to the laser penetrating the tissue, or for indicating when contact has been made between the IMD and the front surface of the tissue. A weakness of the device taught in the '703 patent is the inability to achieve high measurement accuracy when the IMD is very close to, or in contact with, the tissue surface. It would be desirable to accurately determine the IMD proximity to the tissue surface when it is close to the tissue surface, as well as accurately indicating contact with the tissue surface.

SUMMARY OF THE INVENTION

A method and apparatus for remotely monitoring the location of an interventional medical device (IMD) using ultrasonic signals. Both the proximity and alignment of the IMD are calculated from ultrasound signals reflected off the tissue surface. The inclusion of an offset between the distal end of the IMD and the ultrasound transducer enables accurate position and alignment monitoring of when the IMD is in contact with, or very close to, the tissue surface. The timing of the reflected signal is used to measure proximity or contact. A comparison of the strength between multiple reflected signals is used to measure the alignment of the IMD in 3D space or perpendicularity to a given surface. The present invention may be used as a location indicator with a wide variety of IMDs, and in a wide variety of medical procedures.

BRIEF DESCRIPTION OF THE DRAWINGS

FIGS. 2A and 2B are detailed representations of a medical device approaching a tissue surface.

FIGS. 3A and 3B are detailed representations of a medical device being aligned perpendicular to a tissue surface.

DETAILED DESCRIPTION

The present invention is directed to an ultrasound system used to remotely determine proximity and perpendicularity of an interventional medical device (IMD) with respect to a tissue surface. Typically, although not exclusively, the IMD is a tool that is used as part of a minimally invasive surgical (MIS) procedure. MIS procedures, such as laparoscopy, are well known in art. The present invention is not, however, intended to be limited to any particularly surgical procedure. Similarly, the types of IMDs that may be used in conjunction with the present invention is intended to be broad, including, but not limited to, catheters, probes, endoscopes, fiber optic devices, cannules, stylets, needles, laparoscopes and surgical lasers. As used in the present disclosure, the location of an IMD is a general term and consists of both proximity and perpendicularity to a tissue surface. The proximity is a distance between the distal end of an IMD and the tissue surface, which may also be expressed as the state "contact" when the distance is zero. Perpendicularity is a measure of whether or not the longitudinal axis of an IMD, at the distal end of the IMD, is at right angles to the plane of the tissue surface at a point where there is contact between the IMD and the tissue surface, or projected contact along the longitudinal axis. As discussed more fully below, the perpendicularity of an IMD is generally defined in three dimensional (3D) space, often using two orthogonal planes passing through the longitudinal axis of the IMD. Degree of perpendicularity is a synonym for perpendicularity and is used in some instances to further emphasize that perpendicularity is a term of measurement.

One application of the present invention is use with a catheter to perform a transmyocardial revascularization (TMR) procedure. This embodiment is chosen because it well illustrates the present invention and is not intended to indicate a limit of the scope of uses for the present invention. The TMR procedure is well known in the art. TMR involves creating channels in the left ventricle, from inside the heart, to increase the blood and oxygen supply to the heart muscle. Surgical lasers and mechanical devices are some of the many means for creating the channels. Regardless of the channel creating device used, medical personnel operate the device remotely. That is, the distal end of the IMD will be inside the heart.

Figure 1:
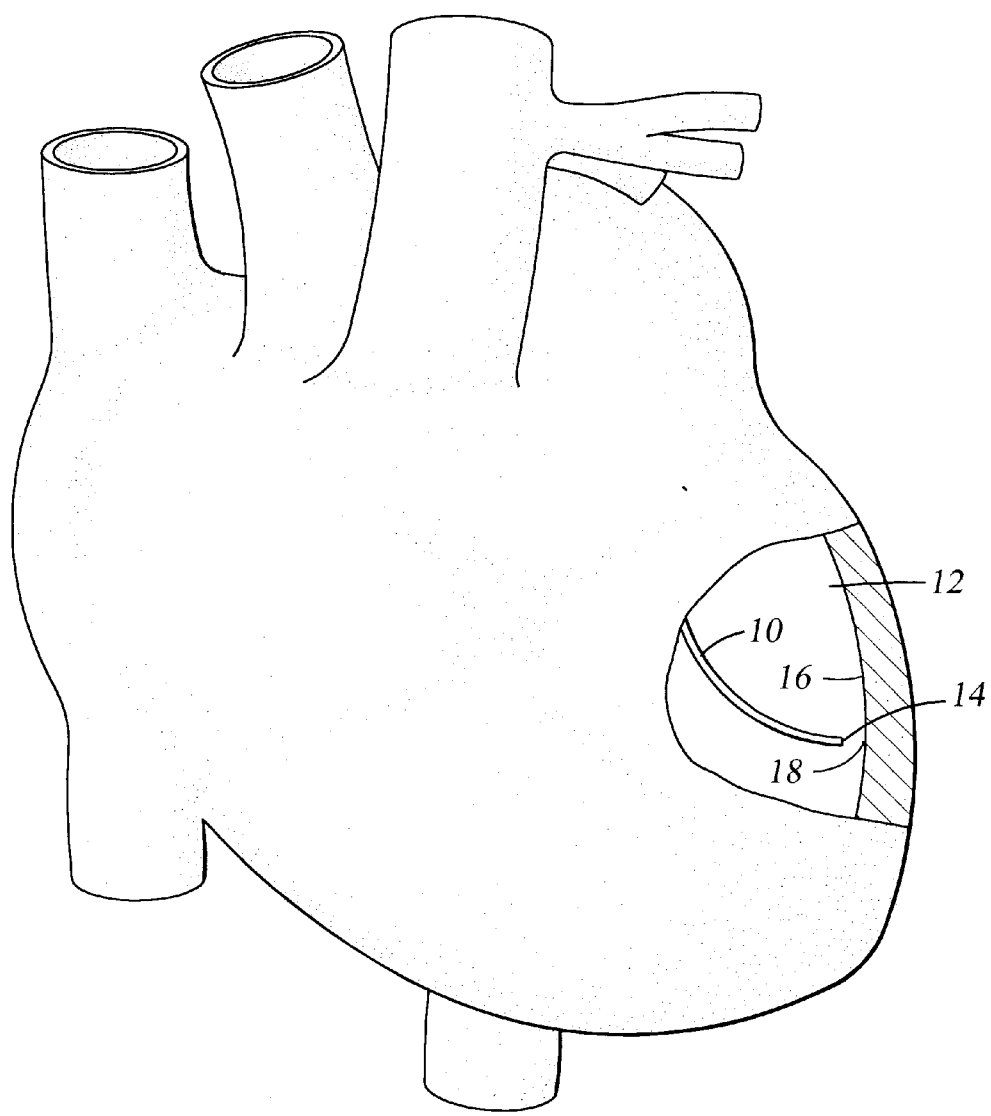
FIG. 1 is a sectional view of a medical device inside a heart.

FIG. 1 is a sectional view of an IMD 10 inside a heart ventricle 12 with the distal end 14 of IMD 10 near the tissue surface 16 at location 18. In order to reach the stage depicted in FIG. 1, medical personnel have had to guide IMD 10 through the patient's blood vessels and into ventricle 12. This global scale guidance of IMD 10 can be accomplished using any of a variety of techniques and is not the objective of the present invention. The present invention is instead directed towards indicating proximity, or contact, between distal end 14 and tissue surface 16 at location 18 and indicating the perpendicularity of distal end 14 with tissue surface 16. In a TMR procedure, prior to beginning the process of creating channels in the heart wall, the physician may like to confirm that distal end 14 is in contact with and perpendicular to, tissue surface 16 at location 18.

As used in this disclosure, the term distal end will be used to describe both the portion of IMD 10 within the patient (e.g., the opposite of the proximal end), and a point at the "tip" of IMD 10, the furthest from the proximal end. Thus, the proximity or distance between distal end 14 and tissue surface 16 corresponds to the distance, measured along a projection of the longitudinal axis of IMD 10, between a point at the extreme end of IMD 10 and tissue surface 16. Although, for clarity, the geometry of the distal end 14 of IMD 10 is shown as a flat surface, perpendicular to the longitudinal axis of IMD 10, the present invention is not intended to be limited to any particular configuration.

FIGS. 2A and 2B are detailed representations of distal end 14 and tissue surface 16 near location 18. The proximity 20 of distal end 14 to tissue surface 16 decreases from FIG. 2A to FIG. 2B as IMD 10 approaches tissue surface 16. The present invention provides a remote indication of the magnitude of proximity 20. Preferably, embodiments of the present invention are configured to clearly indicate when IMD 10 is in contact with tissue surface 16, at location 18, corresponding to a proximity 20 equal to zero.

FIGS. 3A and 3B are also detailed representations of distal end 14 and tissue surface 16 near location 18, depicting the perpendicularity of IMD 10. Within a single plane, such as that depicted in FIG. 3A, a number of possible angular measurements may be used to depict the degree of perpendicularity of IMD 10, relative to tissue surface 16. A few of these possible perpendicularity measurements are noted in FIG. 3A as references 22, 24 and 26. Those of ordinary skill in the art will appreciate that the number of possible perpendicularity measurements is virtually unlimited and the present invention is not intended to be limited to any particular metric. For example, embodiments of the present invention may use direction cosines instead of angular values to indicate perpendicularity. The degree of perpendicularity within a single plane is essentially a measure of how close the orientation of IMD 10 is to that depicted in FIG. 3B, where angles 22 and 26 are both equal to 90°.

Of course, IMD 10 must be oriented in 3D space, not just in a single plane. To depict the perpendicularity in 3D space, an embodiment of the present invention uses perpendicularity measurements in at least two different planes, with each plane passing through the longitudinal axis 28 of IMD 10. Preferably, although not necessarily, the two perpendicularity measurement planes are orthogonal. In one embodiment of the present invention, the perpendicularity measurement planes are oriented so that they are cooperatively aligned with the axes by which IMD 10 is remotely "steered" or controlled. Such steerability of catheters is known in the art. Using such an embodiment, the user will have perpendicularity information directly corresponding to the IMD 10 orientation controls, resulting a highly ergonomic feedback and control system for maneuvering IMD 10.

The present invention uses ultrasound signals reflected off tissue surface 16 for both proximity 20 and perpendicularity measurements. The timing of the reflected signals is used to measure proximity and the reflected signal strengths are used to measure perpendicularity. Using the timing of reflected or echo signals to measure a distance is not new, and determining distance based on the reflected signal is known to those of ordinary skill in the art. Displaying the echo signal amplitude, or signal strength, as a function of the time interval between pulse and echo is a traditional amplitude mode (A-mode) display known to those of ordinary skill in the art. The present invention, unlike the prior art, uses two properties of the reflected signals, the timing and the amplitude, to measure two aspects of the IMD orientation, proximity and perpendicularity. The present invention is particularly suited to indicate contact between distal end 14 and tissue surface 16. As discussed more fully below, prior art methods of measuring the proximity of distal end 14 to tissue surface 16 with ultrasound signals are not well suited for accurately indicating contact.

The perpendicularity, measurement, uses multiple transducers arranged around the circumference of IMD 10. When IMD 10 is perpendicular to a tissue surface at a location 18, as shown in FIG. 3B, the reflected ultrasound signals received at the transducer will be at the maximum amplitude and equal. When IMD 10 is not perpendicular to the tissue surface at location 18, as shown in FIG. 3A, the tissue surface at location 18 causes a portion of the reflected signals to diverge somewhat, resulting in a lower amplitude signal being reflected back to the transducer. Those of ordinary skill in the art, with benefit of the present disclosure, will recognize that timing of the reflected signals will (intrinsically) differ along with the amplitude when IMD 10 is not perpendicular to the tissue surface at location 18.

The present invention compares the strength of the reflected signals, as measured at multiple transducers, to indicate perpendicularity. Because perpendicularity is measured in 3D space, a minimum of three, and preferably four, transducers are used. Embodiments of the present invention may use four transducers spaced at 90° to allow perpendicularity measurements in two orthogonal planes. Preferably, in such a four transducer embodiment, the transducers are aligned so the axes used to steer IMD 10 correspond to the planes used for perpendicularity measurements.

Figure 4A:
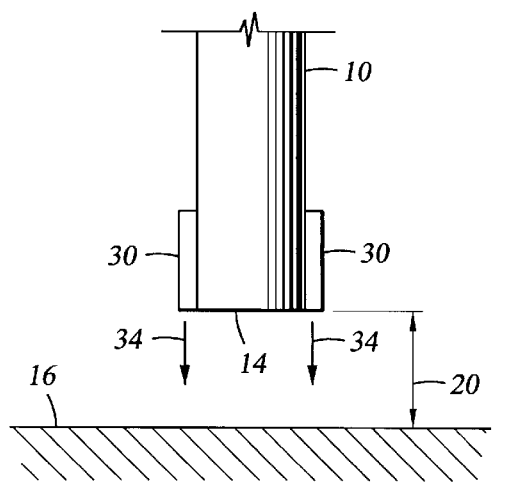
FIGS. 4A and 4B show the prior art and a transducer offset in accordance with an embodiment of the present invention.
Figure 4B:
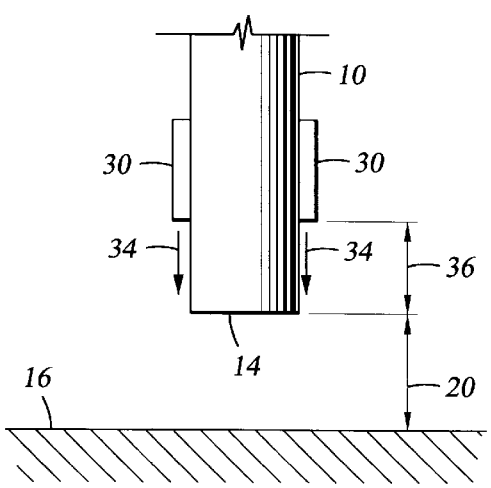

Referring now to FIGS. 4A and 4B, depicting distal end 14 of IMD 10 near tissue surface 16, as measured by proximity 20, the prior art is shown in FIG. 4A and the present invention is shown in FIG. 4B. A pair of ultrasound transducers 30 are shown mounted on IMD 10. Transducers 30 transmit the ultrasound signal 34 and receive the reflection of that signal off of tissue surface 16.

The time for signals 34 to travel ($t_d$) roundtrip over a distance (d) is given by the formula: where $v_m$ is the velocity of the ultrasound signal in the particular media. In FIG. 4A, proximity 20 (and distance d) approaches zero as IMD 10 approaches contact with tissue surface 16, which also causes the travel time $t_d$ of signals 34 to approach zero. On the other hand, in an embodiment of the present invention, as depicted in FIG. 4B, transducers 30 are mounted on IMD 10 with an offset 36 from distal end 14, so that the travel time $t_d$ of signals 34 will never drop below $$\frac{2d}{v_m},$$

where d equals the offset 36 distance, when IMD 10 is in contact with tissue surface 16. This non-zero time period between transmitting and receiving the echo of signal 34 is used to accurately receive and measure the reflection of signal 34 off surface 16 when distal end 14 is close to, or in contact with, tissue surface 16.

Ultrasonic transducers are often reciprocal. That is, the same device may be used to both transmit and receive the acoustic wave signals. However, it is extremely difficult to transmit and receive simultaneously. The phrase "you cannot be listening while you are screaming," applies to electro-mechanical devices such as transducers, as well as humans. This problem may best be addressed by one of two techniques, separating the transmission and detection either spatially (distance) or temporally (time). In the context of MIS procedures generally, and TMR procedures in particular, these choices are limited because the size of IMD 10 is preferably very small (e.g., it must fit inside a blood vessel). With such small devices, it may not be feasible to spatially separate the transmission and detection sufficiently. This physical constraint effectively recommends the temporal separation techniques. In a temporal separation technique, a signal 34 is transmitted, and a finite time later detection of the echo begins.

Figure 5:
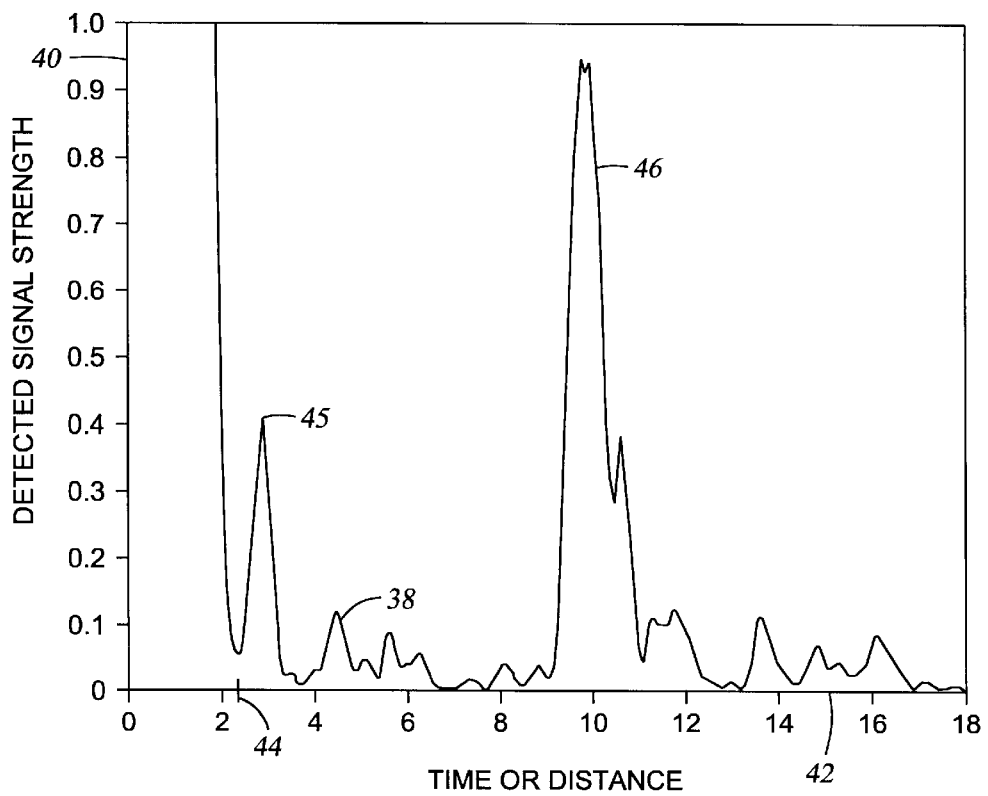
FIG. 5 is a representative plot of an ultrasound echo signal strength versus time or distance.

Referring to FIG. 5, a representative plot of echo signal 38 amplitude 40, as received at transducer 30, versus time or distance 42, where t=0 corresponds to the time when the transmission of signal 34 begins. Those of ordinary skill in the art will recognize that time and distance are equivalent values on such a plot, and are directly related through the value of $v_m$. Prior to a time indicated by reference point 44, the "ringing" caused by the bleed of the transmission makes accurate measurement of echo signal 38 difficult. The present invention uses offset 36 so that when distal end 14 is in contact with tissue surface 16, the travel time of signal 34 exceeds that shown at point 44. Amplitude peak 45 indicates the location of tissue surface 16 relative to distal end 14. Note, peak 46 corresponds to the echo of the ultrasound signal off a second tissue surface, such as the outer well of the heart. Proximity 20 (shown on FIG. 4B) to the first tissue surface 16 will always correspond to the first peak 45.

The location of reference point 44 on axis 40 is dependent on the design characteristics of the particular ultrasound transducers 30, the form of signal 45, and the velocity of sound for ultrasound signals ($v_m$) in the particular media. Preferably, embodiments of the present invention modify offset 36 for various transducer designs and the anticipated signal transmission media(s). The present invention is not, however, intended to be limited to any particular transducer design characteristics use in any particular media, or use with a single media. For TMR procedures, a reference point 44 corresponding to a distance on the order of 2 mm may be used.

Figure 6A:
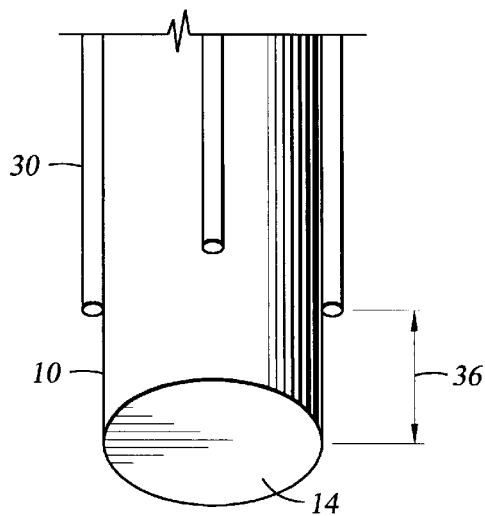
FIGS. 6A through 6D show various transducer configurations in accordance with embodiments of the present invention.
Figure 6B:
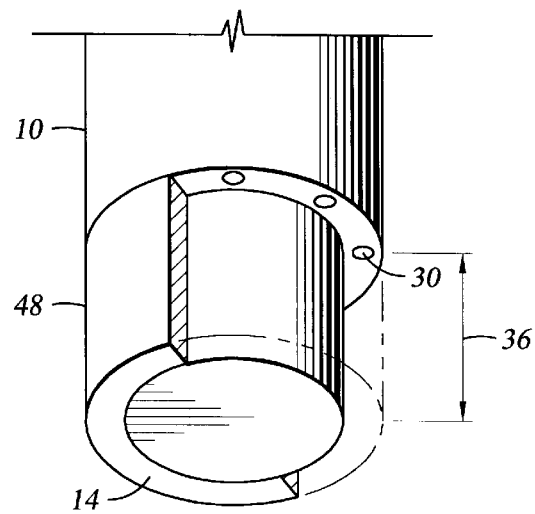
Figure 6C:
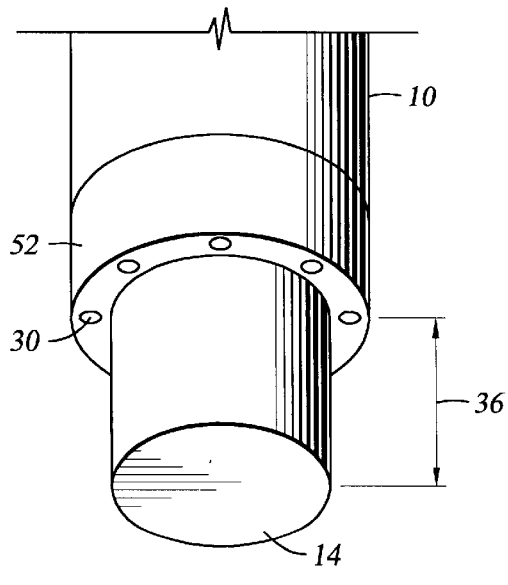
Figure 6D:
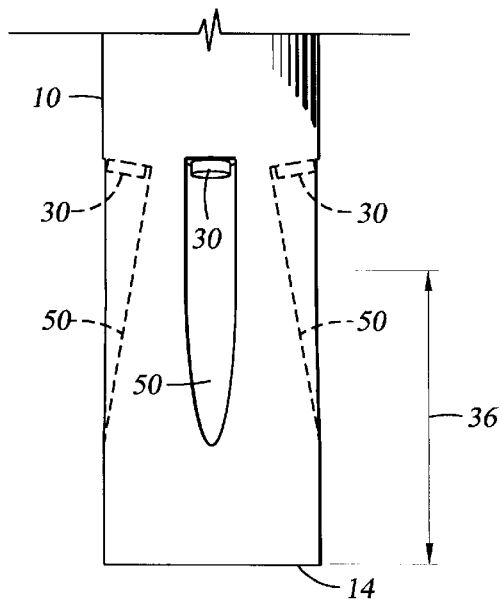

The mounting of transducers 30 on IMD 10 shown in FIGS. 4A and 4B is only one of many possible configurations that might be used with the present invention. Referring now to FIGS. 6A through 6D, four configurations are shown for mounting transducers 30 on a catheter-like IMD 10 with offset 36. FIG. 6A depicts an embodiment with transducers 30 mounted on the external surface of IMD 10. In FIG. 6B, transducers 30 are mounted within IMD 10 with an ultrasonically transparent channel 48 located along the offset 36 between transducers 30 and distal end 14. FIG. 6C is similar to FIG. 6B, but omits channel 48. FIG. 6D mounts transducers 30 within recesses 50, at a slight angle to the longitudinal axis of IMD 10. Those of ordinary skill in the art will recognize that there are many more transducer mounting configurations for catheter-like devices, as well as other types of IMDs 10 than are illustrated in FIGS. 6A through 6D, and the present invention is not intended to be limited to any particular transducer mounting configuration.

As shown in FIG. 6C, embodiments of the present invention may use a transducer ring assembly 52 instead of multiple individual transducers. Often such transducer ring assemblies 52 are less expensive than individual transducers and such rings may only require a single pair of conductors for the entire ring 52, instead of a pair of conductors for each transducer 30.

Those of ordinary skill in the art recognize that ultrasound transducers can be fabricated from a variety of materials, in a variety of shapes, to transmit at a variety of frequencies and amplitudes, and with a variety of signal detection characteristics. The present invention is not intended to be limited to use with any particular transducer design.

Figure 7:
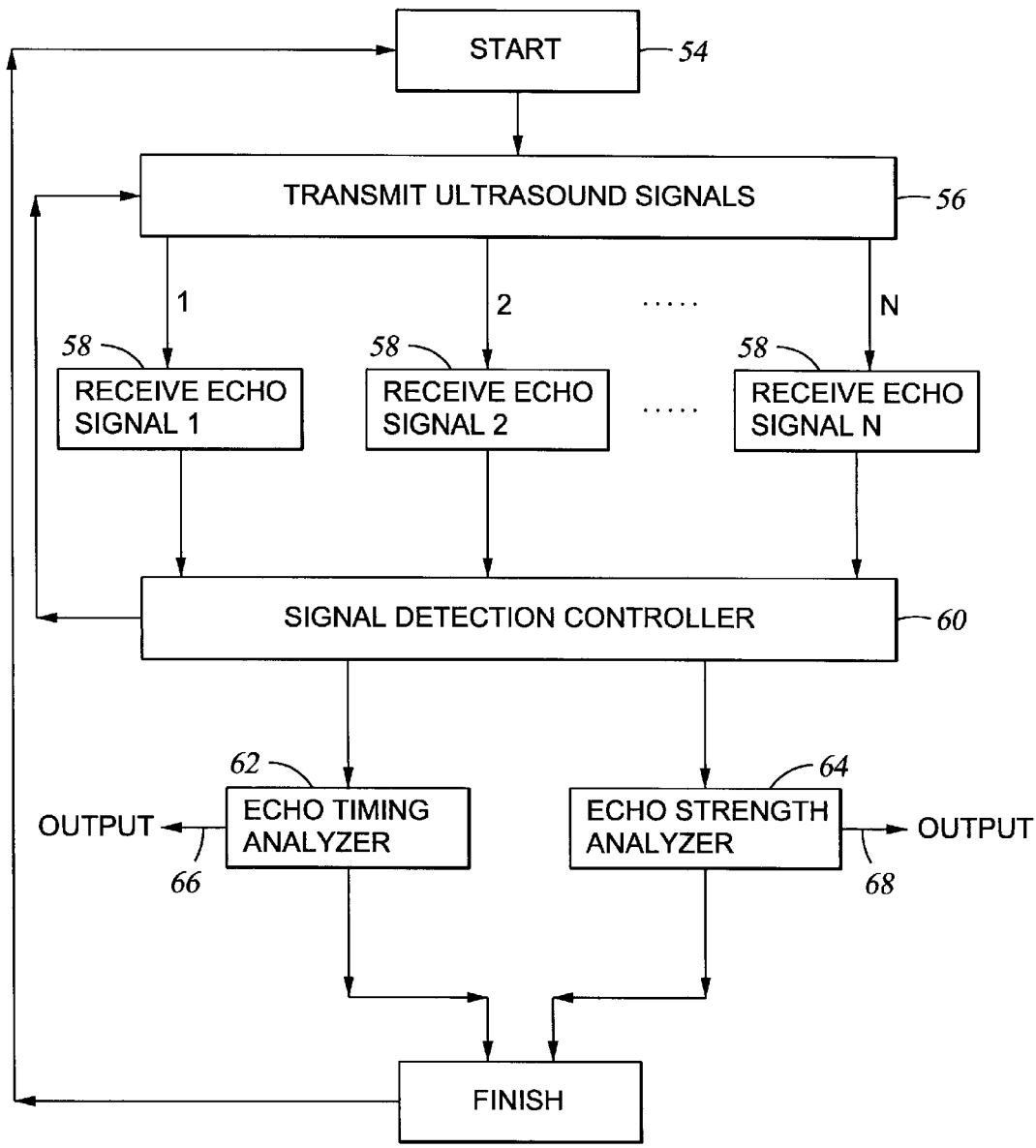
FIG. 7 shows a flow chart for locating an IMD in accordance with an embodiment of the present invention.

FIG. 7 is a flow chart depicting the process followed by an embodiment of the present invention. The process start 54 may be initiated manually, by the system operator, or automatically based on either the passage of time or detecting the location of IMD 10 within a particular area. Multiple transducers transmit an ultrasound signals 56 either simultaneously or in accordance with a predefined firing sequence. Following transmission 56, transceivers 30 attempt to receive the echo signals 58 reflected off tissue surface 16. A signal detector controller 60 receives signal data from the plurality of transducers 30 and controls the re-transmission, if necessary. If a sufficient number of signals are not detected, or are below a minimum signal strength, such as when distal end 14 is too far from tissue surface 16, the transmit step 56 is repeated. Controller 60 passes the received echo signal data to echo timing analyzer 62 and echo strength analyzer 64 for proximity and degree of perpendicularity calculations, respectively, and output reporting 66 and 68. The calculations and reporting are preferably performed in real-time or near real-time, with the entire process repeated continuously. Echo timing analyzer 62 may use the echo signal from either a single or a plurality of transducers 30 to calculate proximity. Those of ordinary skill in the art will recognize that using multiple signals is a technique to increase the accuracy of the proximity measurement process.

Echo strength analyzer 64 requires signals from at least two transducers in order to calculate perpendicularity in a single plane. Embodiments of the present invention may compare two pairs of echo signals from three transducers 30, two or more pairs of echo signals from four transducers 30, or virtually any combination of signals from a ring of transducers 30 to calculate perpendicularity. In one embodiment, perpendicularity is calculated and displayed in the planes corresponding to the steering axes of IMD 10.

Figure 8A:
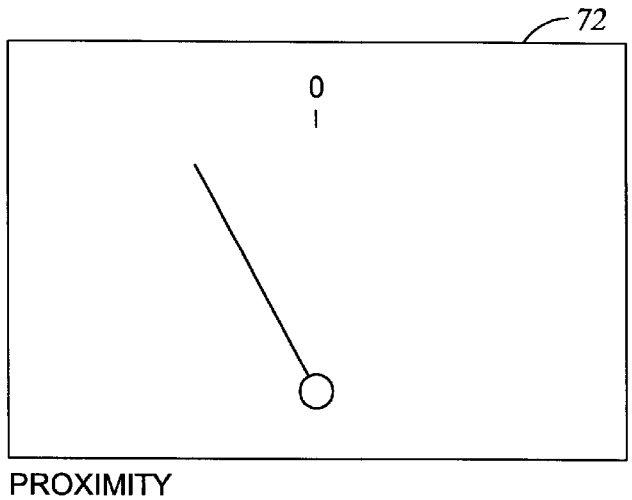
FIG. 8 is an illustration of a sample user interface for displaying the measurements made in accordance with an embodiment of the present invention.
Figure 8B:
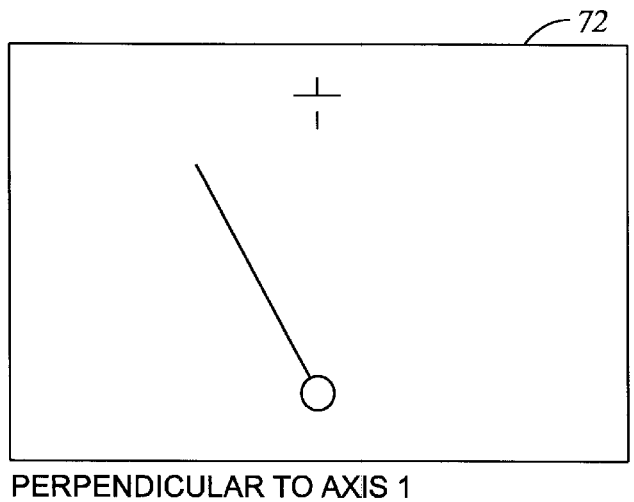
Figure 8C:
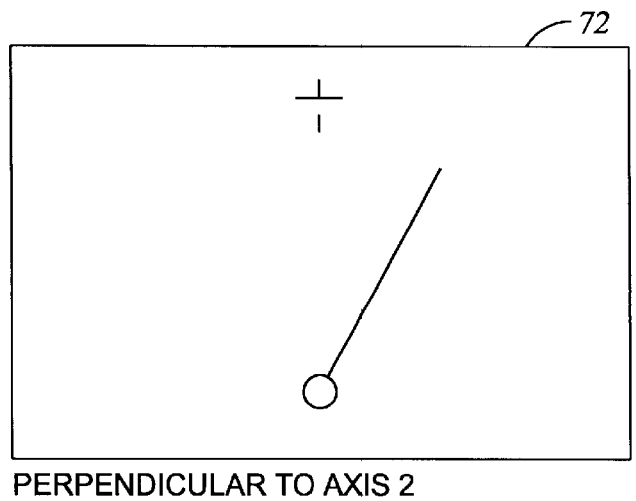

There are many ways the proximity and perpendicularity information may be presented to the user, and the present invention is not intended to be limited to any particular user interface. One embodiment of a user interface 70 for use with the present invention is shown in FIG. 8. Proximity indicator 72 uses a needle gauge with a mark on the face of the gauge indicating contact between IMD 10 and tissue surface 16. Perpendicularity indicators 74 and 76 also use needle gauges to indicate when IMD 10 is perpendicular along a first and second axis respectively. Measurement calibration graduations could be added to any, or all, of the gauges. Other types of indicators such as light emitting diodes (LEDs), rows of lights, digital displays, and audio signals could also be used with the present invention to indicate proximity and perpendicularity measurements to the user.

While a user interface, like interface 70, is used with one embodiment of the present invention, it is expected that a variety of different user interface formats will be used in conjunction with the present invention. Those of ordinary skill in the art will be familiar with designing a user interface to accept output signals 66 and 68 from the present invention as input to the user interface. Preferably, the user interface is highly customized to the particular application in which it will be used. The present invention is not, however, intended to be limited to any particular user interface design and it is recognized that there are many ways to present proximity and perpendicularity information to the user.

Figure 9A:
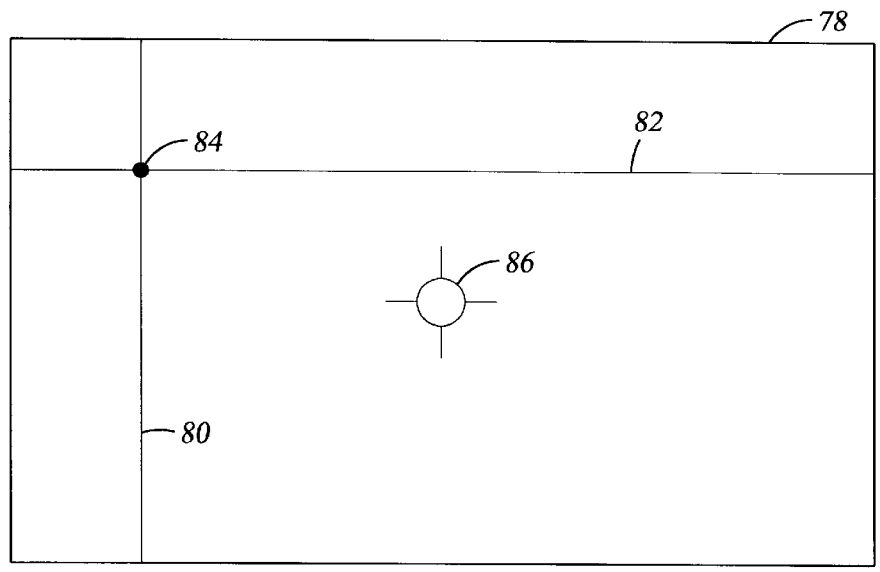
FIGS. 9A and 9B are illustrations of other user interfaces for displaying the measurements made in accordance with an embodiment of the present invention.

In one embodiment of the present invention illustrated in FIG. 9A, the perpendicularity along two axes are displayed simultaneously. Dual axis perpendicularity indicator 78 uses two movable supports 80 and 82, corresponding to the perpendicularity along two respective axes. The intersection of movable supports 80 and 82 is the current perpendicularity position dot 84, which moves relative to bullseye 86. When IMD 10 is perpendicular to tissue surface 16 along both axes, dot 84 is aligned with bullseye 86.

Figure 9B:
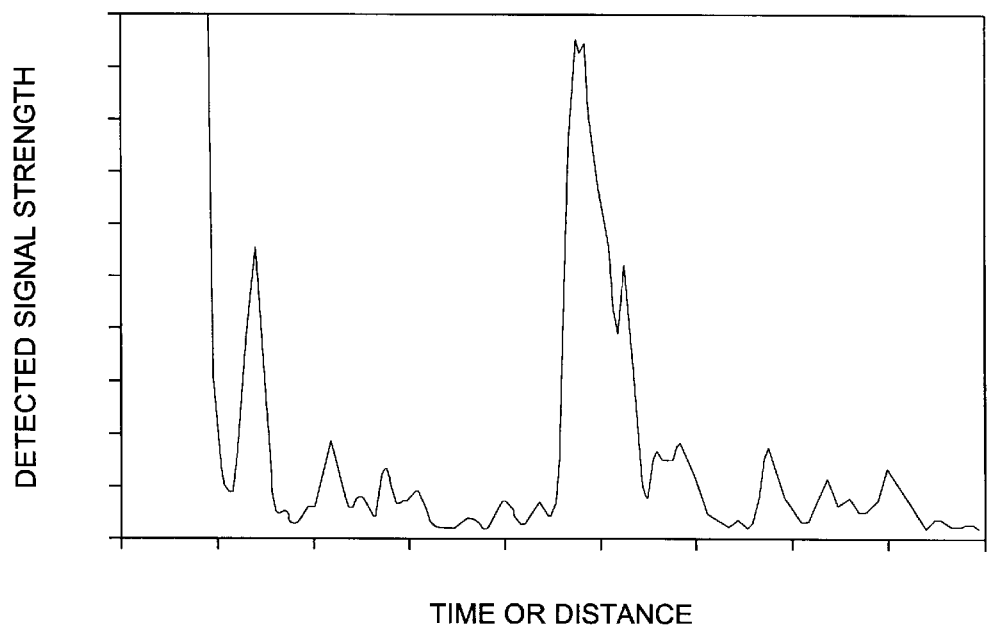

Another embodiment of the present invention also displays proximity adjacent to dual axis perpendicularity indicator 78. This embodiment may display an A-mode graph, similar to that shown in FIG. 5 and shown here in FIG. 9B, directly below indicator 78.

While embodiments and applications of this invention have been shown and described, it would be apparent to those skilled in the art, after a review of this disclosure, that many more modifications than mentioned above are possible without departing from the inventive concepts herein. The invention, therefore, is not to be restricted except in the spirit of the appended claims.

What is claimed is:

1. A method of monitoring the position of a longitudinal axis, of an, interventional medical device (IMD) relative to a tissue surface, comprising:

transmitting at least three ultrasound signals toward the tissue surface, where the signals travel in a direction which is substantially parallel to the longitudinal axis of the IMD;

detecting a plurality of echo signals reflected off the tissue surface;

analyzing an elapsed time between said transmitting and said detecting to measure proximity of said IMD to the tissue surface; and comparing a signal strength or time delay in receipt of the echo among the at least three echo signals to measure perpendicularity of the longitudinal axis of the IMD to the tissue surface.

2. A method in accordance with claim 1, wherein:

measuring perpendicularity is performed along two orthogonal planes.

3. A method in accordance with claim 2, further comprising:

reporting said proximity and perpendicularity.

4. An apparatus to monitor the position of an interventional medical device (IMD) relative to a tissue surface, comprising:

an IMD with a transducer ring assembly mounted on the IMD at an offset distance from the distal end of the IMD, aligned to transmit signals substantially a longitudinal axis of the IMD toward the distal end of the IMD and receive echo signals reflected off the tissue surface, where the transducer ring assembly transmits at least three signals toward the tissue surface;

a signal detection controller coupled to said transducer ring for routing the echo signals received by the transducer ring;

an echo timing analyzer coupled to the controller, for measuring proximity; and an echo strength analyzer coupled to the controller, for measuring perpendicularity.

5. A method of monitoring a perpendicularity of a distal end of an interventional medical device (IMD) relative to a tissue surface, comprising:

transmitting at least three ultrasound signals from said IMD toward the tissue surface, wherein the signals are transmitted substantially parallel to a longitudinal axis of the IMD;

receiving at least three echos which correspond with said at least three ultrasound signals, which signals are reflected from the tissue surface; and comparing said at least three echos which correspond with said at least three signals, to determine a degree of perpendicularity of said distal end of said IMD relative to the tissue surface.

6. A method in accordance with claim 5, wherein said at least three ultrasound signals are transmitted simultaneously from said IMD toward the tissue surface.

7. A method in accordance with claim 5, wherein said signals are transmitted from a transducer-containing device so that said at least three signals emanate from a plane which is essentially perpendicular to said longitudinal axis of said IMD, but travel in a direction which is substantially parallel to said longitudinal axis of said IMD.

8. A method in accordance with claim 5, wherein proximity and perpendicularity of said distal end of said IMD relative to said tissue surface are determined without interference in said echo signals due to closeness to or contact of said distal end of said IMD with said tissue surface, wherein said transducer-containing device is set back from said distal end of said IMD a distance sufficient to permit the transmitted signal amplitude to decay below the amplitude of an echo signal reflected off the tissue surface when the tissue surface is in contact with the distal end of the IMD.

9. A method in accordance with claim 8, further including an additional step in which a position of said distal end of said IMD relative to the tissue surface is adjusted and a second set of at least three ultrasonic signals is transmitted toward the tissue surface, a second set of at least three echos is received, and a second degree of perpendicularity of said distal end of said IMD relative to the tissue surface is determined.

10. A method in accordance with claim 9, wherein said additional step is repeated a number of times to improve perpendicularity.

11. A method in accordance with claim 5, further including an additional step in which a position of said distal end of said IMD relative to the tissue surface is adjusted and a second set of at least three ultrasonic signals is transmitted toward the tissue surface, a second set of at least three echos is received, and a second degree of perpendicularity of said distal end of said IMD relative to the tissue surface is determined.

12. A method in accordance with claim 11, wherein said additional step is repeated a number of times to improve perpendicularity.

13. An apparatus to monitor the position of a longitudinal axis of an interventional medical device (IMD) relative to a tissue surface, comprising:

an IMD including an ultrasonic transducer device which transmits a signal from at least three different locations around the periphery of longitudinal axis of the IMD, where the ultrasonic transducer device is mounted in a manner so that signals from the ultrasonic transducer device travel in a direction which is substantially, parallel to the longitudinal axis of the IMD, wherein the ultrasonic transducer device is capable of both transmitting the ultrasonic signal and receiving an echo from the reflected signal; and an echo signal strength analyzer which compares the echo strength relative to the original ultrasonic signal to determine perpendicularity of the longitudinal axis of the IMD relative to the tissue surface.

14. An apparatus in accordance with claim 13, wherein said transducers transit a signal which emanates from a plane which is essentially perpendicular to the longitudinal axis of the IMD.

15. An apparatus in accordance with claim 13, wherein the ultrasonic transducer device is mounted on the IMD at an offset distance from a distal end of the IMD.

16. An apparatus in accordance with claim 15, further comprising:

an echo timing analyzer to determine the proximity of the distal end of the IMD to the tissue surface.

17. An apparatus in accordance with claim 16, wherein the echo signal strength analyzer and the echo timing analyzer are coupled to a signal detection controller.

18. An apparatus in accordance with claim 13, wherein said signal strength measured is an amplitude.

19. A method of positioning a longitudinal axis of an interventional medical device (IMD) to be perpendicular to a tissue surface, comprising:

a) transmitting a signal in the form of an annular ultrasound wave toward the tissue surface, wherein the signal travels in a direction which is substantially parallel to the longitudinal axis of the IMD;

b) measuring an amplitude of an echo signal reflected off the tissue surface, c) repeating steps a) and b) until a maximum amplitude is obtained, indicating that the IMD is perpendicular to the tissue surface.

* * * * *